US006210684B1

(12) United States Patent
Stanford et al.

(10) Patent No.: US 6,210,684 B1
(45) Date of Patent: Apr. 3, 2001

(54) METHOD FOR DELAYING THE ONSET OF AIDS

(75) Inventors: John Lawson Stanford, Marden; Graham Arthur William Rook, Haverhill, both of (GB)

(73) Assignee: Stranford Rock Limited (GB)

( * ) Notice: Subject to any disclaimer, the term of this patent is extended or adjusted under 35 U.S.C. 154(b) by 0 days.

(21) Appl. No.: 08/442,298

(22) Filed: May 16, 1995

Related U.S. Application Data

(63) Continuation of application No. 08/312,673, filed on Sep. 28, 1994, now abandoned, which is a continuation of application No. 08/031,307, filed on Mar. 15, 1993, now abandoned, which is a continuation-in-part of application No. 07/820,684, filed on Mar. 27, 1992, now abandoned.

(30) Foreign Application Priority Data

Sep. 14, 1992 (GB) .................................................. 9219425
Jul. 28, 1998 (GB) .................................................. 8917256

(51) Int. Cl.[7] .......................... A61K 39/04; A61K 39/00; A61K 39/38
(52) U.S. Cl. ...................................... 424/248.1; 424/184.1
(58) Field of Search .............................. 424/248.1, 184.1

(56) References Cited

U.S. PATENT DOCUMENTS 4,724,144 * 2/1988 Rook et al. ............................ 424/88

OTHER PUBLICATIONS

Källenius, et al, 1989, "Does Vaccination with Bacille . . . ." Reviews of Infect. Dis. 11(2):349–351.*
Brown, 1993, "AIDS Vaccine Trials Viewed With Caution" The Washington Post, Jun. 10.*
Haseltine, 1988, "Replication and Pathogenesis of . . . ." J. Acquired Imm. Def. Syndromes 1(3): 217–240.*
Festenstein, et al, 1991, "Tuberculosis and the . . . ." J. Applied Bacteriology 71: 19–30.*
Michihiko, et al, 1989, "Augmentation of in–vitro . . . ." The Lancet May 27, 1989, 1206–1207.*
Stanford, et al, 1991, "Is Africa Lost", The Lancet 338: 557–558.*

* cited by examiner

Primary Examiner—Jeffrey Stucker
Assistant Examiner—Brett Nelson
(74) Attorney, Agent, or Firm—Pillsbury Winthrop LLP

(57) ABSTRACT

Antigenic and/or immunoregulatory material derived from *Mycobacterium vaccae* is useful for delaying the onset of AIDS with or without associated tuberculosis.

5 Claims, No Drawings

METHOD FOR DELAYING THE ONSET OF AIDS

This is a continuation of application Ser. No. 08/312,673, filed on Sep. 28, 1994, which was abandoned upon the filing hereof which is a continuation of application Ser. No. 08/031,307, filed on Mar. 15, 1993 (abandoned), which is a continuation-in-part of application Ser. No. 07/820,686, filed on Mar. 27, 1992 now abandoned.

This invention relates to the prophylaxis and therapy of AIDS (acquired immune deficiency syndrome).

BACKGROUND OF THE INVENTION

The causative agent for AIDS is known to be a virus of the retrovirus family called HIV (human immunodeficiency virus). Infection with HIV does not, however, immediately give rise to overt symptoms of AIDS. The only indication of exposure to the virus may be the presence of antibodies thereto in the blood of an infected subject who is then described as 'HIV positive'. The infection may lie dormant, giving rise to no obvious symptoms, and the incubation period prior to development of AIDS may vary from several months to decades. Development of AIDS itself may be preceded by the AIDS-related complex (ARC) which is characterised by unexplained fever, weight loss, chronic cough or diarrhoea.

The reasons for the variable period between infection with the virus and breakdown of the immune system in an infected individual are poorly understood. Factors at present unknown may trigger proliferation of the virus with consequential disruption of the immune system. The victims of the disease are then subject to various infections and malignancies which, unchecked by the disabled immune system, lead to death.

Despite the rapid growth of research into AIDS no vaccine against it is yet available. It has been suggested that the genetic variability of the virus will in fact hamper the search for an effective vaccine.

The association between HIV infection and tuberculosis is well known. An early effect of HIV infection is the reactivation of previously dormant tubercule bacilli. The maintenance of resistance to mycobacteria is an active immunological process which is compromised by HIV infection. In dually infected persons, there is a high reactivation rate of dormant tubercule bacilli and this reactivation usually occurs well before the appearance of other HIV/AIDS-related infections which strongly suggests that an important effect of HIV infection is to destroy precisely those immune functions, presumably T-cell mediated, that maintain mycobacterial dormancy.

There is also evidence that where active tuberculosis is superimposed on HIV infection, there is a dramatic loss of CD4 T-cells which results in very rapid development of overt symptoms of AIDS. It appears in fact that immune mediators released in tuberculosis accelerate transactivation of the HIV provirus.

We have previously described the use of antigenic and/or immuno regulatory material derived from *Mycobacterium vaccae* in the treatment of tuberculosis (see, for example, British Patent No. 2156673 and U.S. Pat. No. 4,724,144).

SUMMARY OF THE INVENTION

We have now discovered that the same therapeutic agent not only delays development of AIDS in patients infected by HIV, but also is capable of causing regression, or even removal, of overt symptoms of AIDS even in patients where the disease is far advanced. These effects have been found in patients suffering also from tuberculosis, but are expected to occur also in patients who are suffering from HIV infection with or without AIDS and without associated tuberculosis.

The present invention accordingly provides a method for the prophylaxis or therapy of AIDS comprising administering to a subject who has been exposed to HIV infection or is HIV positive with or without overt symptoms of AIDS, killed cells of *Mycobacterium vaccae* in an amount sufficient to provoke an immune response effective to delay or prevent onset, or reduce the severity, of AIDS. The subject may or may not also show overt symptoms of tuberculosis.

DETAILED DESCRIPTION OF THE INVENTION

Therapeutic agents which may be used in the present invention comprise dead cells of *M. vaccae*, preferably cells which have been killed by autoclaving. The immunotherapeutic agent normally comprises more than $10^8$ microorganisms per ml of diluent, and preferably from $10^8$ to $10^{11}$ killed *M. vaccae* microorganisms per ml of diluent.

The diluent may be pyrogen-free saline for injection alone, or a borate buffer of pH 8.0. The diluent should be sterile. A suitable borate buffer is:

| | |
|---|---|
| $Na_2B_4O_7 \cdot 10H_2O$ | 3.63 g |
| $H_3BO_3$ | 5.25 g |
| NaCl | 6.19 g |
| Tween | 0.0005% |
| Distilled Water | to 1 litre |

The preferred strain of *M. vaccae* is one denoted R877R isolated from mud samples from the Lango district of Central Uganda (J. L. Stanford and R. C. Paul, Ann. Soc. Belge Med, Trop. 1973, 53, 389). The strain is a stable rough variant and belongs to the aurum sub-species. It can be identified as belonging to *M. vaccae* by biochemical and antigenic criteria (R. Bonicke, S. E. Juhasz., Zentr albl. Bakteriol. Parasitenkd. Infection skr. Hyg. Abt. 1, Orig., 1964, 192, 133).

The strain denoted R877R has been deposited at the National Collection of Type Cultures (NCTC) Central Public Health Laboratory, Colindale Avenue, London NW9 5HT, United Kingdom on Feb. 13, 1984 under the number NCTC 11659.

For the preparation of an immunotherapeutic agent which may be used in the method of the present invention, the microorganism *M. vaccae* may be grown on a suitable solid medium. A modified Sauton's liquid medium is preferred (S. V. Boyden and E. Sorkin., J. Immunol, 1955, 75, 15) solidified with agar.

Preferably the solid medium contains 1.3% agar. The medium inoculated with the microorganisms is incubated aerobically to enable growth of the microorganisms to take place, generally at 32° C. for 10 days. The organisms are harvested, then weighed and suspended in a diluent. The diluent may be unbuffered saline but is preferably borate-buffered and contains a surfactant such as Tween 80 as described above. The suspension is diluted to give 100 mg of microorganism/ml. For further dilution, borate buffered saline is preferably used so that the suspension contains 10 mg wet weight of microorganisms/ml of diluent. The suspension may then be dispensed into 5 ml multidose vials. Although the microorganisms in the vials may be killed using irradiation e.g. from $^{60}$Cobalt at a dose of 2.5 megarads, or by any other means, for example chemically, it is preferred to kill the microorganisms by autoclaving, for example at 10 psi for 10 minutes (115°–125° C.). It has been discovered that autoclaving yields a more effective preparation than irradiation.

The immunotherapeutic agent is in general administered by injection in a volume in the range 0.1–0.2 ml, preferably 0.1 ml, given intradermally. A single dosage will generally contain from $10^7$ to $10^{10}$ killed *M. vaccae* microorganisms. It is preferred to administer to patients a single dose containing $10^8$ to $10^9$ killed *M. vaccae*. However, the dose may be repeated depending on the condition of the patient.

Although the immunotherapeutic agent will generally be administered by intradermal injection, other routes, e.g. oral administration, can also be used.

For 20 to 50% of African patients with HIV infection tuberculosis is the first symptom in development of AIDS. Tuberculosis infection is associated with significant production of interleukin 6 (IL6) and tumour necrosis factor (TNF). There is evidence to show that the addition of TNF and IL6 to HIV-infected T cells in vitro leads to increased multiplication of the virus. The TNF release associated with tuberculosis infection in an HIV-positive subject may precipitate proliferation of the HIV with consequential disruption of the function of T4 cells in the immune system and production of immunodeficiency.

It is believed that the prevention of tuberculosis or, more specifically, the inhibition of TNF, and IL6 associated (Koch) responses, will have a delaying effect on precipitation of the AIDS syndrome. The agents of the invention are believed to exert an immunomodulatory effect on pre-existent cell mediated necrotizing responses, changing them to a non-necrotizing form of response and it is believed that this is due to decreased production of, or a change in function of, IL6 and TNF. It is also believed that protective immunity against both tuberculosis and leprosy is enhanced.

Among a group of patients being treated for tuberculosis were seventeen who were seropositive by the Wellcome ELISA for HIV1. All the patients were prescribed streptomycin, isoniazid, rifampicin and pyrazinamide for their tuberculosis. Therapy was abbreviated and did not last longer than three months in any case. Eight of the seventeen patients received the therapeutic agent of the present invention and nine received placebo (saline). At follow up about one year later only three of the patients who had received only the anti-tuberculosis drugs had survived and all three of these had advanced tuberculosis. Seven of the eight patients treated with the therapeutic agent of the present invention had become sputum smear negative for acid fast bacilli (i.e. tubercule bacilli) and the general improvement in their condition was similar to that in tuberculosis patients who were not HIV positive. Five of the eight patients had generalised lymphadenopathy at the time of diagnosis. This had resolved at the time of follow-up. The two patients who were retested serologically at the follow-up were found to be negative for HIV1.

It may be advantageous and is within the scope of the invention to use more than one strain of *M. vaccae,* and/or to include in the therapeutic agent other mycobacterial antigens. Tuberculin may also be included.

The therapeutic agent may also contain BCG (Bacillus Calmette-Guerin) vaccine, in particular the freeze-dried form of the vaccine, to promote its effect.

The therapeutic agent can contain further ingredients such as adjuvants, preservatives, stabilizers etc. It may be supplied in sterile injectable liquid form or in sterile freeze-dried form which is reconstituted prior to use.

*M. vaccae* may be used as such or as an extract or fractionated portion of the organism to prepare therapeutic agents according to the invention.

The following Example describes the preparation of a therapeutic agent as used in the invention.

EXAMPLE

*M. vaccae* is grown on a solid medium comprising modified Sauton's medium solidified with 1.3% agar. The medium is inoculated with the microorganism and incubated for 10 days at 32° C. to enable growth of the microorganism to take place. The microorganisms are then harvested and weighed and suspended in diluent to give 100 mg of microorganisms/ml of diluent. The suspension is then further diluted with buffered saline to give a suspension containing 10 mg wet weight of microorganisms/ml of diluent and dispensed into 5 ml multidose vials. The vials containing the live microorganism are then autoclaved for 10 minutes at 10 psi to kill the microorganisms and give the immunotherapeutic agent of the invention, which may (if desired) be further diluted for use.

This immunotherapeutic agent may be administered by intradermal injection in the manner already described.

What is claimed is:

1. A method for delaying the onset of AIDS comprising administering to an HIV positive subject, killed cells of *Mycobacterium vaccae* in an amount effective to delay the onset of AIDS.

2. A method according to claim 1, wherein the cells of *M. vaccae* have been killed by autoclaving.

3. A method according to claim 1, wherein the cells are of the strain deposited at the National Collection of Type Cultures (NCTC) Central Public Health Laboratory, Colindale Avenue, London NW9 5HT, United Kingdom on Feb. 13, 1984 under the number NCTC 11659.

4. A method according to claim 1, wherein the killed cells of *M. vaccae* are present in an amount comprising from $10^7$ to $10^{10}$ microorganisms per dose.

5. A method according to claim 1 wherein the subject suffers from tuberculosis.

\* \* \* \* \*

UNITED STATES PATENT AND TRADEMARK OFFICE
CERTIFICATE OF CORRECTION

PATENT NO. : 6,210,684 B1
DATED : April 3, 2001
INVENTOR(S) : Stanford et al.

It is certified that error appears in the above-identified patent and that said Letters Patent is hereby corrected as shown below:

<u>Title page,</u>
Item [73], Assignee, delete "Stranford Rock Limited (GB)" and insert -- Stanford Rook Limited (GB) --.

Item [30], Foreign Application Priority Data, please correct the filing date of British priority application No. 8917256 as follows:
Delete "Jul. 28, 1998" and insert -- Jul. 28, 1989 --.
Please insert as the third and fourth priority applications as follows:
Insert -- Jul. 27, 1990    (ZA)............................. 90/5927
           Jul. 27, 1990       ......................... PCT/GB90/01169 --.

Signed and Sealed this

Twenty-sixth Day of November, 2002

Attest:

Attesting Officer

JAMES E. ROGAN
*Director of the United States Patent and Trademark Office*